United States Patent [19]

Asakawa

[11] Patent Number: 4,659,509

[45] Date of Patent: Apr. 21, 1987

[54] AROMA COMPOSITION

[75] Inventor: Yoshinori Asakawa, Tokushima, Japan

[73] Assignee: Kuraray Co., Ltd., Kurashiki, Japan

[21] Appl. No.: 724,118

[22] Filed: Apr. 17, 1985

[30] Foreign Application Priority Data

Apr. 27, 1984 [JP] Japan ................................ 59-87440
Aug. 21, 1984 [JP] Japan ............................... 59-174766

[51] Int. Cl.$^4$ ........................... A61K 7/46; C11B 9/00
[52] U.S. Cl. ................................ 252/522 R; 568/819; 549/560
[58] Field of Search ................... 252/522 R; 549/560; 568/819

[56] References Cited

U.S. PATENT DOCUMENTS 3,703,479 11/1972 Theimen ............................ 568/819
3,767,713 10/1973 Theimen ............................ 568/819

OTHER PUBLICATIONS

House et al., "Journal American Chemical Society", vol. 82 (1960), pp. 639–640.
Chemical Abstracts, vol. 100, No. 25, Jun. 18, 1984, p. 320, Abstract No. 206508p.
Tetrahedron Lett. 1984, 25(13), 1401-2.

*Primary Examiner*—Werren B. Lone
*Attorney, Agent, or Firm*—Oblon, Fisher, Spivak, McClelland & Maier

[57] ABSTRACT

There is provided an aroma composition containing a sesquiterpene alcohol having the hexahydroindane skeleton. Such sesquiterpene alcohol has a fantastic aroma reminiscent of a variety of odors based on the woody note and powdery green note and furthermore has high diffusivity and retentivity and accords well with a number of perfume and fragrance materials and flavor materials.

6 Claims, No Drawings

AROMA COMPOSITION

BACKGROUND OF THE INVENTION

1. Field of the Invention

This invention relates to an aroma composition containing a sesquiterpene alcohol having the hexahydroindane skeleton. The invention also relates to a novel sesquiterpene alcohol having the hexahydroindane skeleton.

2. Description of the Prior Art

As a fragrance raw material isolable from lichens, there is known the oak moss oil, which is obtained, for example, from *Evernia prunastri*, a kind of lichen growing on oak. The oil is used as a fixer for perfume and fragrances of the chypre or fougère type, for instance.

The present inventor conducted an intensive study of terpene compounds contained in various lichens and mosses and previously, in collaboration with Joseph D. Connolly and his colleagues, succeeded in isolating a so-far unknown sesquiterpene alcohol, 3,7-dimethyl-2-(2-methyl-1-propenyl)hexahydroindan-2-ol, from a species of moss, *Frullania tamarisci* subsp. *tamarisci*, which is found widely in Europe. [This sesquiterpene alcohol is called tamariscol; cf. Tetrahedron Letters, 25 (13), 1401-1402 (1984).]

Furthermore, it is known that indane compounds such as 5-acetyl-1,1,2,3,3,6-hexamethylindane and 4-acetyl-6-tert-butyl-1,1-dimethylindane have a musk-like animal note and are usable as perfume and fragrance materials for use in soap and cosmetics.

An object of the invention is to provide the use, as perfume and fragrance materials and flavor materials, of certain sesquiterpene alcohols having the hexahydroindane skeleton and a characteristic odor distinct from that of so-far known indene compounds.

Another object of the invention is to provide one of said sesquiterpene alcohols which is a novel compound.

These objects as well as other objects and advantages of the invention will become apparent to those skilled in the art from the following detailed description.

SUMMARY OF THE INVENTION

The invention thus provides an aroma composition which contains a sesquiterpene alcohol having the general formula

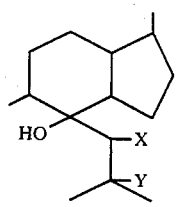

(I)

wherein X and Y combinedly represent a carbon-carbon bond or an epoxy group (—O—).

The invention also provides a sesquiterpene alcohol of the above general formula (I) wherein X and Y combinedly represent an epoxy group (—O—), namely 3,7-dimethyl-2-(2-methyl-1,2-epoxypropyl)hexahydroindan-2-ol (hereinafter referred to as epoxytamariscol).

DETAILED DESCRIPTION OF THE INVENTION

The sesquiterpene alcohol of the above general formula (I) includes the following two compounds:

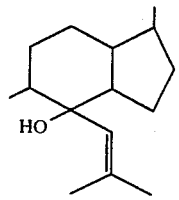 and 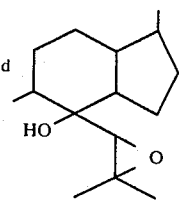

Tamariscol    Epoxytamariscol

The above-mentioned moss *Frullania tamarisci* subsp. *tamarisci*, which contains tamariscol, belongs to the family Frullaniaceae of the order Jungermanniales of the class Hepaticae, is a cormus moss growing on the tree trunk or a moist rock bed and can be easily collected. Furthermore, *Frullania tamarisci* subsp. *tamarisci* is distributed widely in Europe and it is possible to secure it in a sufficient quantity for use as a raw material on a commercial scale.

Tamariscol can be obtained, for example, by extraction of dried and ground *Frullania tamarisci* subsp. *tamarisci* with a solvent such as an ether (e.g. diethyl ether, dibutyl ether), a halogenated hydrocarbon (e.g. methylene chloride, chloroform, dichloroethane) or an alcohol (e.g. methanol, ethanol, isopropyl alcohol). The extraction is generally conducted at a temperature of about 20°-40° C. over about 1-3 days. Removal of the solvent from the extract by distillation gives the oil of *Frullania tamarisci* subsp. *tamarisci* which contains tamariscol. Tamariscol can be isolated in the conventional manner by subjecting the oil to distillation or column chromatography using silica gel. The above-mentioned oil can also be obtained by subjecting *Frullania tamarisci* subsp. *tamarisci* to steam distillation or supercritical extraction with carbon dioxide gas, which is carried out by a conventional method. The oil obtained by steam distillation can be directly used as perfume and fragrance materials and flavor materials.

Epoxytamariscol is produced by subjecting tamariscol to ordinary epoxidation reaction. For instance, treatment of tamariscol with hydrogen peroxide, an organic peroxide such as tert-butyl hydroperoxide, or an organic peracid such as peracetic acid, perbenzoic acid or m-chloroperbenzoic acid gives epoxytamariscol. Such hydrogen peroxide, organic peroxide or organic peracid is used in an amount of about 0.1-2 moles, preferably about 0.9-1.2 moles, per mole of tamariscol. The reaction is generally carried out in a solvent, such as an alcohol (e.g. methanol, ethanol), an ether (e.g. diethyl ether, tetrahydrofuran), acetone, a hydrocarbon (e.g. hexane, benzene, toluene), a halogenated hydrocarbon (e.g. methylene chloride, 1,2-dichloroethane), etc. The solvent is used in an amount of about 2-100 parts by weight per part by weight of tamariscol. In cases where hydrogen peroxide or an organic peroxide is used, the reaction is carried out at a temperature ranging from about −50° C. to the boiling point of the solvent used, preferably at room temperature or in the vicinity thereof, if necessary in the presence of vanadium pentoxide or vanadium oxyacetylacetonate complex, for instance. When an organic peracid is used, the reaction is carried out at a temperature of about −50° C. to 50° C., preferably about 0°–30° C. After the reaction, sodium hydrogen sulfite is added to the reaction mixture to treat the remaining hydrogen peroxide, organic peroxide or peracid therewith, and the mixture is then treated by a usual separation procedure, which can isolate epoxytamariscol. For example, the reaction mixture after the above treatment with sodium hydrogen sulfite is extracted with a solvent such as diethyl ether etc., the extract is washed with water and dried over anhydrous magnesium sulfate, and the solvent is then distilled off, whereby epoxytamariscol can be obtained.

Tamariscol has a fantastic aroma reminiscent of a variety of odors based on the woody note and powdery green note, such as the odors of moss, foin, fluvia, costus, violet leaf, marin, etc.

Epoxytamariscol has an aroma of the chypre and oriental type based on the very powdery woody note accompanied by the moss-green note and the aroma is reminiscent of a variety of odors, such as the odors of patchouli, vetiver, oak moss, costus, etc.

In this manner, the sesquiterpene alcohols of general formula (I) have a fantastic aroma reminiscent of a variety of odors based on the woody note and powdery green note and, moreover, have high diffusivity and retentivity and accord well with a number of perfume and fragrance materials, hence they are useful as raw materials for perfume and fragrances.

The sesquiterpene alcohols of general formula (I) can be added to perfume and fragrance compositions in their pure forms or they can be added to mixtures of materials in fragrance-imparting compositions to provide a desired fragrance character to a finished perfume material. The perfume and fragrance compositions obtained according to this invention are suitable in a wide variety of perfumed articles and can also be used to enhance, modify or reinforce natural fragrance materials. It will thus be appreciated that the sesquiterpene alcohols of general formula (I) each are useful as olfactory agents and fragrances.

The term "perfume and fragrance composition" is used herein to mean a mixture of compounds, including, for example, natural oils, synthetic oils, alcohols, aldehydes, ketones, esters, lactones, and frequently hydrocarbons which are admixed so that the combined odors of the individual components produce a pleasant or desired fragrance. Such perfume and fragrance compositions usually contain (a) the main note or the bouquet or foundation-stone of the composition, (b) modifiers which round off and accompany the main note, (c) fixatives which include odorous substances which lend a particular note to the composition throughout all stages of evaporation, and substances which retard evaporation, and (d) top notes which are usually low-boiling fresh-smelling materials. Such perfume and fragrance compositions of this invention can be used in conjunction with carriers, vehicles, solvents, dispersants, emulsifiers, surface-active agents, aerosol propellants and the like.

In perfume and fragrance compositions, the individual components contribute their particular olfactory characteristics, but the overall effect of the perfume and fragrance composition will be the sum of the effect of each ingredient. Thus, the sesquiterpene alcohols of general formula (I) can be used alone or in combination to alter the aroma characteristics of a perfume and fragrance composition, for example, by highlighting or moderating the olfactory reaction contributed by another ingredient of the composition.

The perfume and fragrance composition according to this invention contains an olfactorily sensible amount of the sesquiterpene alcohols of general formula (I). The proportion of the sesquiterpene alcohols of general formula (I) in the total composition may vary according to the intended use of the composition; for example, it may range from about 0.005 weight percent to 95 weight percent. The perfume and fragrance composition of this invention can be used in a large variety of ways. For example, it can be used as or in soaps; space deodorants; perfumes and eau de cologne; cosmetic preparations such as lotions, creams, etc.; bath supplies such as bath oil, bath salts, etc.; hair preparations such as hair tonics, pomades, hair liquids, hair creams, stick pomades, shampoos, rinses, etc.; cleansers; detergents, etc. In addition, the perfume and fragrance composition can also be used for scenting such substrates as textile fibers and fabrics, paper products and so on.

The sesquiterpene alcohols of general formula (I) are also useful as ingredients for the preparation of artificial flavors and as flavor additives in foodstuffs, animal feeds, beverages, pharmaceutical preparations and tobacco products. The term "foodstuff" is used in this specification in its broadest sense and is meant to include also products such as coffee, tea and cocoa.

When the sesquiterpene alcohols of general formula (I) are used as flavoring agents or additives for modifying the organoleptic properties of foodstuffs, animal feeds, beverages, pharmaceutical preparations and tobacco products, said sesquiterpene alcohols can be used in proportions which, again, vary within wide limits. Interesting flavoring effects, for instance, can be achieved by using the sesquiterpene alcohols of general formula (I) in proportions from 0.1 to 10 ppm based on the weight of the products to be flavored. However, these proportions can be increased beyond 10 ppm up to about 100 ppm in order to achieve special flavoring effects. In the preparation of flavoring compositions by admixing the sesquiterpene alcohols to other aromatics, the said compounds can be used, for example, in proportions of about 0.1% to about 15% of the total weight of the flavoring composition. In many cases average proportions of about 1 to 10% by weight will give the desired results.

The above-mentioned aroma composition provided by this invention has a modern and high-quality note which is making the best use of the aroma of each of sesquiterpene alcohols of general formula (I).

The following examples are given to merely illustrate this invention in further detail and should by no means be construed as limiting the scope of the invention.

EXAMPLE 1

A dry substance (1 kg) of *Frullania tamarisci* subsp. *tamarisci*, which was collected in Scotland, was extracted with 3 l of diethyl ether at 20° C. for 24 hours. Removal of the solvent from the extract by distillation gave 50 g of a crude product, which was subjected to column chromatography using 300 g of silica gel (eluent system: n-hexane-ethyl acetate). The ethyl acetate (10%)-hexane (90%) eluate gave 1 g of a colorless, viscous oil. The instrumental analysis data for this oil are given below. These instrumental analysis data identified said oil as 3,7-dimethyl-2-(2-methyl-1-propenyl)-hexahydroindan-2-ol.

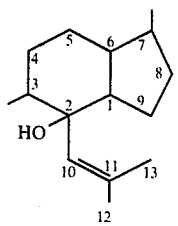

Specific rotation $[\alpha]_D$: +19.7 (c 1.1, CHCl$_3$)
Molecular weight: 222 [M+]
Infrared (IR) absorption spectrum, $\nu_{max}$(CCl$_4$): 3,620 cm$^{-1}$ Nuclear magnetic resonance (NMR) spectrum:

$^1$H-NMR (360 MHz) $\delta_{ppm}^{CHCl_3}$: 5.07 (m, J=1.3 Hz, 1H-10); 1.88 (d, J=1.2 Hz, 3H-13); 1.75 (d, J=1.5 Hz, 3H-12); 0.92 (d, J=6.6 Hz, 3H-15); 0.88 (d, J=6.6 Hz, 3H-14).

$^{13}$C-NMR (50 MHz) $\delta_{ppm}^{CHCl_3}$: 59.0 (C-1), 79.0 (C-2), 46.0 (C-3), 33.3 (C-4), 30.6 (C-5), 50.3 (C-6), 40.1 (C-4), 32.2 (C-8), 24.3 (C-9), 121.9 (C-10), 136.4 (C-11), 28.5 (C-12), 20.3 (C-13), 15.4 (C-14), 19.2 (C-15).

EXAMPLE 2

Synthesis of epoxytamariscol

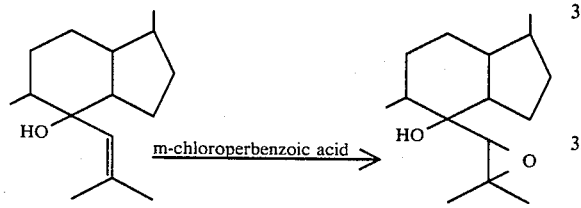

Tamariscol (346 mg, 1.56 mmol) was dissolved in 10 ml of methylene chloride and, to this solution, there was added dropwise a solution of 259 mg (1.51 mmol) of m-chloroperbenzoic acid in 5 ml of methylene chloride, followed by stirring at room temperature for 1 hour. Thereafter, 10 ml of a saturated aqueous solution of sodium hydrogen sulfite was added to the reaction mixture. The resultant mixture was stirred for 1 hour and then extracted with 50 ml of diethyl ether. The extract was washed in sequence with aqueous sodium hydrogen carbonate and aqueous sodium chloride and dried over anhydrous magnesium sulfate, and the solvent was then distilled off to give 359 mg (1.51 mmol) of epoxytamariscol. The yield was 97%. The instrumental analysis data for the product are given below.

Mass spectrum (m/z): 238 [M+]

$^1$H-NMR spectrum (90 MHz) $\delta_{ppm}^{CDCl_3}$: 0.85–0.96 (m, 6H); 1.21 (bs, 1H); 1.45, 1.41 (each s, 6H); 2.56–2.59 (s, 1H).

IR spectrum (CCl$_4$, cm$^{-1}$): 3570, 1460, 1380, 1300, 1240, 1120, 1090, 1060, 1035, 1020, 990, 950, 905, 865, 845, 670.

EXAMPLE 3

Perfume and Fragrance Composition of the Fantastic Chypre Type

A perfume and fragrance composition having a fantastic chypre note was prepared according to the following formula:

|  | Parts by weight |
| --- | --- |
| Bergamot oil | 20 |
| Oak moss oil | 25 |
| Geranium oil | 5 |
| Violet leaf oil | 1 |
| Benzyl acetate | 5 |
| Linalool | 5 |
| Hydroxycitronellal | 5 |
| Eugenol | 3 |
| Sandalwood oil | 2 |
| Vetiver oil | 3 |
| Methyl ionone | 2 |
| Rose absolute | 3 |
| Jasmin absolute | 2 |
| Labdanum resin | 5 |
| Amber tink | 5 |
| Musk ambrette | 4 |
| Tamariscol | 5 |
|  | 100 |

EXAMPLE 4

Perfume and Fragrance Composition of the Fougère Type

A perfume and fragrance composition having a fougère note was prepared according to the following formula:

|  | Parts by weight |
| --- | --- |
| Bergamot oil | 15 |
| Lavender oil | 15 |
| Oak moss oil | 6 |
| Amyl salicylate | 2 |
| Fluvia oil | 2 |
| Costus oil | 3 |
| Patchouli oil | 2 |
| Geranium oil | 5 |
| Linalool | 3 |
| Citronellol | 2 |
| Tonka resin | 5 |
| Coumarin | 18 |
| Musk ambrette | 4 |
| Vetiverol | 3 |
| Musk tink | 3 |
| Tolu balsam | 2 |
| Vanillin | 1 |
| Jasmin absolute | 3 |
| Tamariscol | 6 |
|  | 100 |

EXAMPLE 5

Perfume and Fragrance Composition of the Fancy Violet Type

A perfume and fragrance composition having a fancy violet note was prepared according to the following formula:

|  | Parts by weight |
| --- | --- |
| α-Ionone | 25 |
| Methyl ionone | 15 |
| Ylang ylang oil | 5 |
| Violet leaf absolute | 3 |
| Bergamot oil | 3 |
| Phenylethyl alcohol | 8 |
| Methyl heptin carbonate | 5 |
| Cyclamen aldehyde | 3 |
| Benzyl acetate | 5 |
| Anisaldehyde | 5 |
| Aldehyde C-12 MNA 10% | 3 |
| Vetiverol | 2 |
| Foin Coupe oil | 1 |

|  | Parts by weight |
| --- | --- |
| Cassie oil | 1 |
| Heliotropine | 4 |
| Jasmin absolute | 2 |
| Rose absolute | 2 |
| Tamariscol | 8 |
|  | 100 |

EXAMPLE 6

Perfume and Fragrance Composition of the Chypre Type

A perfume and fragrance composition having a chypre note was prepared according to the following formula:

|  | Parts by weight |
| --- | --- |
| Bergamot oil | 20 |
| Lavender oil | 2 |
| Oak moss oil | 10 |
| Geranium oil | 3 |
| Orange flower oil | 2 |
| Amyl salicylate | 3 |
| Phenylethyl alcohol | 5 |
| Citronellol | 5 |
| Linalool | 5 |
| Methyl ionone | 5 |
| Benzyl acetate | 3 |
| Rose absolute | 2 |
| Jasmin absolute | 3 |
| Patchouli oil | 5 |
| Vetiver oil | 2 |
| Sandalwood oil | 3 |
| Coumarin | 5 |
| Vanillin | 2 |
| Amber synthetic | 5 |
| Musk synthetic | 5 |
| Epoxytamariscol | 5 |
|  | 100 |

EXAMPLE 7

Perfume and Fragrance Composition of the Oriental Bouquet Type

A perfume and fragrance composition having an oriental bouquet note was prepared according to the following formula:

|  | Parts by weight |
| --- | --- |
| Bergamot oil | 15 |
| Carnation absolute | 5 |
| Ylang ylang oil | 3 |
| Neroli oil | 3 |
| Geranium oil | 2 |
| Aldehyde C-10 10% | 3 |
| Aldehyde C-11 10% | 3 |
| α-Ionone | 7 |
| Methyl ionone | 5 |
| Iris oil | 2 |
| Eugenol | 4 |
| Rose base | 7 |
| Jasmin base | 8 |
| Hydroxycitronellol | 5 |
| Patchouli oil | 5 |
| Heliotropine | 2 |
| Amber synthetic | 3 |

|  | Parts by weight |
| --- | --- |
| Musk synthetic | 3 |
| Civet tink | 2 |
| Sandalwood oil | 2 |
| Vetiver oil | 3 |
| Epoxytamariscol | 8 |
|  | 100 |

EXAMPLE 8

Perfume and Fragrance Composition of the White Rose Type

A perfume and fragrance composition having a white rose-like note was prepared according to the following formula:

|  | Parts by weight |
| --- | --- |
| Rhodinol | 30 |
| Phenylethyl alcohol | 10 |
| Phenylethyl acetate | 7 |
| Linalool | 10 |
| Geraniol | 10 |
| Bergamot oil | 5 |
| Citronellyl acetate | 3 |
| Aldehyde C-10 10% | 2 |
| Aldehyde C-12 MNA 10% | 3 |
| Rose absolute | 5 |
| Rose synthetic | 5 |
| Patchouli oil | 1 |
| Rosephenone | 2 |
| Musk tink | 2 |
| Epoxytamariscol | 5 |
|  | 100 |

What is claimed is:

1. An aroma composition, comprising an olfactorily sensible amount of 3,7-dimethyl-2-(2-methyl-1,2-epoxypropyl)hexahydroindan-2-ol.

2. A perfume and fragrance composition, comprising an olfactorily sensible amount of 3,7-dimethyl-2-(2-methyl-1-propenyl)hexahydroindan-2-ol.

3. 3,7-Dimethyl-2-(2-methyl-1,2-epoxypropyl)hexahydroindan-2-ol.

4. A process for imparting an aromatic fragrance to a substrate material, comprising the step of:

adding an olfactorily sensible amount of a sesquiterpene alcohol of the general formula:

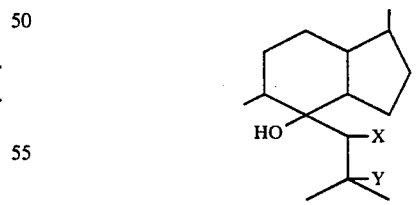

to said substrate material, wherein X and Y taken together represent a carbon-carbon bond or an epoxy group (—O—).

5. The process of claim 4, wherein said sesquiterpene alcohol is 3,7-dimethyl-2-(2-methyl-1-propenyl)hexahydroindan-2-ol.

6. The process of claim 4, wherein said sesquiterpene alcohol is 3,7-dimethyl-2-(2-methyl-1,2-epoxypropyl)hexahydroindan-2-ol.

* * * * *

UNITED STATES PATENT AND TRADEMARK OFFICE
CERTIFICATE OF CORRECTION

PATENT NO. : 4,659,509
DATED : April 21, 1987
INVENTOR(S) : YOSHINORI ASAKAWA

It is certified that error appears in the above-identified patent and that said Letters Patent is hereby corrected as shown below:

Col. 1, line 39, change "indene" to --indane--.

Col. 5, line 13, change "Molecular weight" to --Mass spectrum (m/z)--.

Col. 5, line 22, change "40.1(c-4)" to --40.1(C-7)--.

Signed and Sealed this

Nineteenth Day of April, 1988

Attest:

DONALD J. QUIGG

Attesting Officer

Commissioner of Patents and Trademarks